(12) United States Patent
Kutra et al.

(10) Patent No.: US 10,244,993 B2
(45) Date of Patent: Apr. 2, 2019

(54) COMPRESSION AND SHIELDING DEVICE

(71) Applicant: KONINKLIJKE PHILIPS N.V., Eindhoven (NL)

(72) Inventors: Dominik Benjamin Kutra, Hamburg (DE); Thomas Buelow, Grosshansdorf (DE); Cristian Lorenz, Hamburg (DE); Daniel Bystrov, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 200 days.

(21) Appl. No.: 15/127,570

(22) PCT Filed: Mar. 25, 2015

(86) PCT No.: PCT/EP2015/056360
§ 371 (c)(1),
(2) Date: Sep. 20, 2016

(87) PCT Pub. No.: WO2015/150180
PCT Pub. Date: Oct. 8, 2015

(65) Prior Publication Data
US 2017/0143283 A1 May 25, 2017

(30) Foreign Application Priority Data
Apr. 2, 2014 (EP) .................... 14163122

(51) Int. Cl.
*A61B 6/10* (2006.01)
*A61B 6/04* (2006.01)
*A61B 6/00* (2006.01)

(52) U.S. Cl.
CPC ............ *A61B 6/0414* (2013.01); *A61B 6/107* (2013.01); *A61B 6/502* (2013.01)

(58) Field of Classification Search
CPC ........... A61B 6/00; A61B 6/04; A61B 6/0414; A61B 6/10; A61B 6/107; A61B 6/502; A61B 6/587; A61B 6/589
(Continued)

(56) References Cited

U.S. PATENT DOCUMENTS

| 4,618,973 A | 10/1986 | Lasky |
| 5,189,686 A | 2/1993 | Hixson, Sr. |

(Continued)

FOREIGN PATENT DOCUMENTS

| DE | 102011076823 | 12/2012 |
| EP | 2095771 | 9/2009 |

(Continued)

OTHER PUBLICATIONS

Weinmann, et al., "Collimator design for a dedicated molecular breast imaging-guided biopsy system: proof-of-concept", Med Phys, Jan. 2013; 40(1).

*Primary Examiner* — Jurie Yun
(74) *Attorney, Agent, or Firm* — Larry Liberchuk

(57) ABSTRACT

The present invention relates to a compression and shielding device (10) for X-ray mammography, an X-ray mammography system, and a method for X-ray mammography. The compression and shielding device (10) for X-ray mammography comprises a compression element (11), and a shielding (12). The compression element (11) is arranged to compress a part of the breast to be examined. The shielding (12) is to be arranged between an X-ray source (2) and the compression element (11) to shield an uncompressed part of the breast from the X-ray radiation. The shielding (12) is formed to allow the direction of X-ray radiation to the compressed part of the breast and to keep an uncompressed part of the breast uncovered.

12 Claims, 4 Drawing Sheets

(58) Field of Classification Search
USPC .................................. 378/37, 204, 205, 208
See application file for complete search history.

(56) References Cited

U.S. PATENT DOCUMENTS

| | | | |
|---|---|---|---|
| 5,999,836 A | 12/1999 | Nelson et al. | |
| 7,440,539 B2* | 10/2008 | Danielsson | A61B 6/107 378/147 |
| 7,502,441 B2* | 3/2009 | Lebovic | A61B 6/0414 378/208 |
| 2006/0093084 A1 | 5/2006 | Gutman | |
| 2013/0158389 A1 | 6/2013 | O'Connor | |

FOREIGN PATENT DOCUMENTS

| | | |
|---|---|---|
| WO | 01/66013 | 9/2001 |
| WO | 03/073939 | 9/2003 |
| WO | 2014/001925 | 1/2014 |

* cited by examiner

COMPRESSION AND SHIELDING DEVICE

CROSS REFERENCE TO RELATED APPLICATIONS

This application is the U.S. National Phase application under 35 U.S.C. § 371 of International Application No. PCT/EP2015/056360, filed Mar. 25, 2015, published as WO 2015/150180 on Oct. 8, 2015, which claims the benefit of European Patent Application Number 14163122.6 filed Apr. 2, 2014. These applications are hereby incorporated by reference herein.

FIELD OF THE INVENTION

The present invention relates to a compression and shielding device for X-ray mammography, an X-ray mammography system, and a method for X-ray mammography.

BACKGROUND OF THE INVENTION

Usually, for breast cancer screening an X-ray mammography image of a breast is evaluated for suspicious areas that may indicate a tumor in the tissue of the breast.

For acquiring the X-ray mammography image, the breast may be compressed and flattened between two compression paddles and an X-ray detector arrangement with a digital detector may radiograph the breast, may generate X-ray image data and the X-ray image data may be displayed on the screen of a workstation connected to the X-ray detector. A physician then may investigate and evaluate the displayed X-ray image.

WO 2014/001925 A1 relates to a compression element for a breast holding arrangement for mammography examinations. The compression element comprises a supporting structure, a first surface and a second surface. The supporting structure is configured to be attached to a mounting structure for exerting a compression force on a breast under examination. The first and second surfaces are attached to the support structure; and the first and second surfaces are arranged facing in opposite directions. The second surface is provided to compress the breast under examination.

For further information about the tissue of the breast, magnification views using only local compression are a common technique to further investigate unclear and suspicious findings. In contrast to an X-ray mammogram that aims at compressing and imaging the complete breast, magnification views are executed with the breast compressed only in the region of interest. However, also the uncompressed portions of the breast tissue are still exposed to radiation which increases the total glandular dose.

SUMMARY OF THE INVENTION

It may be an object of the invention to generate an X-ray mammography image of a breast, wherein only the compressed region of interest is exposed to radiation.

The object of the present invention is solved by the subject-matters of the independent claims, wherein further embodiments are incorporated in the dependent claims. It should be noted that the following described aspects of the invention apply also for the compression and shielding device for X-ray mammography, the X-ray mammography system, and the method for X-ray mammography.

According to the present invention, a compression and shielding device for X-ray mammography is presented. It comprises a compression element and a shielding. The compression element is arranged to compress a part of the breast to be examined. The shielding is to be arranged between an X-ray source and the compression element to shield an uncompressed part of the breast from the X-ray radiation. The shielding is formed to allow the direction of X-ray radiation to the compressed part of the breast and to keep an uncompressed part of the breast uncovered.

In other words, the compression and shielding device allows extremely low dose acquisitions by shielding uncompressed parts of the breasts from radiation. Thereby, the total dose for this type of examination is minimized.

Preferably, the compression and shielding device is formed to contact the breast to be examined only by the compression element. The shielded breast portion shall be surrounded by compressed breast portions. Preferably, the compression and shielding device is formed to be slightly and elastically impressed into the breast tissue, and then to be at least partially surrounded not only by flat breast tissue, but also by breast tissue swelling towards the X-ray source.

The compression element may comprise a circumferential edge to contact the breast. The circumferential edge may be circular, oval or angled. The compression element may be disc-shaped or comprise of a disc. The diameter or width of the compression element may be between about 16 cm to 1 cm, preferably between about 10 cm to 2 cm, and more preferably between about 5 cm to 3 cm.

The compression element may be a spot compression element suitable to compress only a part of the breast to be examined. The compressed part of the breast may have a volume between about 3500 $cm^3$ to 1 $cm^3$, preferably between about 1000 $cm^3$ to 8 $cm^3$, and more preferably between about 200 $cm^3$ to 27 $cm^3$.

The compression element may also be one of two compression paddles. The compression element may be the movable or the fixed of two compression paddles. The shielding may be arranged on the upper compression paddle in the direction of the X-ray source, while both compression paddles surround the breast to be examined.

Preferably, the shielding is connected with the compression element.

The shielding may be of arbitrary shape and e.g. cone shaped. The cone may have a circular, oval or angled cross section. The shielding may further be opaque to X-ray radiation. The compression element is transparent to X-ray radiation.

According to the present invention, also an X-ray mammography system is presented. It comprises an X-ray source, an X-ray detector, a breast support, a compression element, and a shielding. The X-ray source is arranged to direct X-ray radiation to a breast to be examined or, in other words, to an area in which the breast can be arranged. The X-ray source is arranged outside the breast to be examined.

The X-ray detector is arranged to detect X-ray radiation having passed through the breast to be examined. The breast support is arranged to support the breast to be examined. The compression element is arranged to compress a part of the breast to be examined. The shielding is arranged between the X-ray source and the compression element to shield an uncompressed part of the breast from the X-ray radiation. The shielding is further formed to allow the direction of X-ray radiation to the compressed part of the breast and to keep an uncompressed part of the breast uncovered.

Preferably, the breast support comprises a positioning element to position the breast closer to the X-ray source than without the positioning element. The positioning element may be arranged below the breast support. The positioning element may be a separate element or integrated into the breast support. The positioning element is movable towards the X-ray source from a lower to an upper position. By moving the positioning element and thereby the breast support towards the X-ray source into the upper position, the breast is lifted towards the X-ray source, which allows a magnification image of the breast compared to lower position.

According to the present invention, also a method for X-ray mammography is presented. It comprises the steps of (not necessarily in this order):

a) arranging a breast to be examined on a breast support, b) compressing a part of the breast to be examined in a compression element, c) arranging a shielding between an X-ray source and the compression element to shield an uncompressed part of the breast from the X-ray radiation, and d) conducting an examination of the compressed part of the breast.

The shielding is arranged between the X-ray source and the compression element to shield an uncompressed part of the breast from the X-ray radiation. The shielding is further formed to allow the direction of X-ray radiation to the compressed part of the breast and to keep an uncompressed part of the breast uncovered.

It shall be understood that the compression and shielding device for X-ray mammography, the X-ray mammography system, and the method for X-ray mammography according to the independent claims have similar and/or identical preferred embodiments, in particular, as defined in the dependent claims. It shall be understood further that a preferred embodiment of the invention can also be any combination of the dependent claims with the respective independent claim.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the accompanying drawings.

DETAILED DESCRIPTION OF EMBODIMENTS

Figure 1:
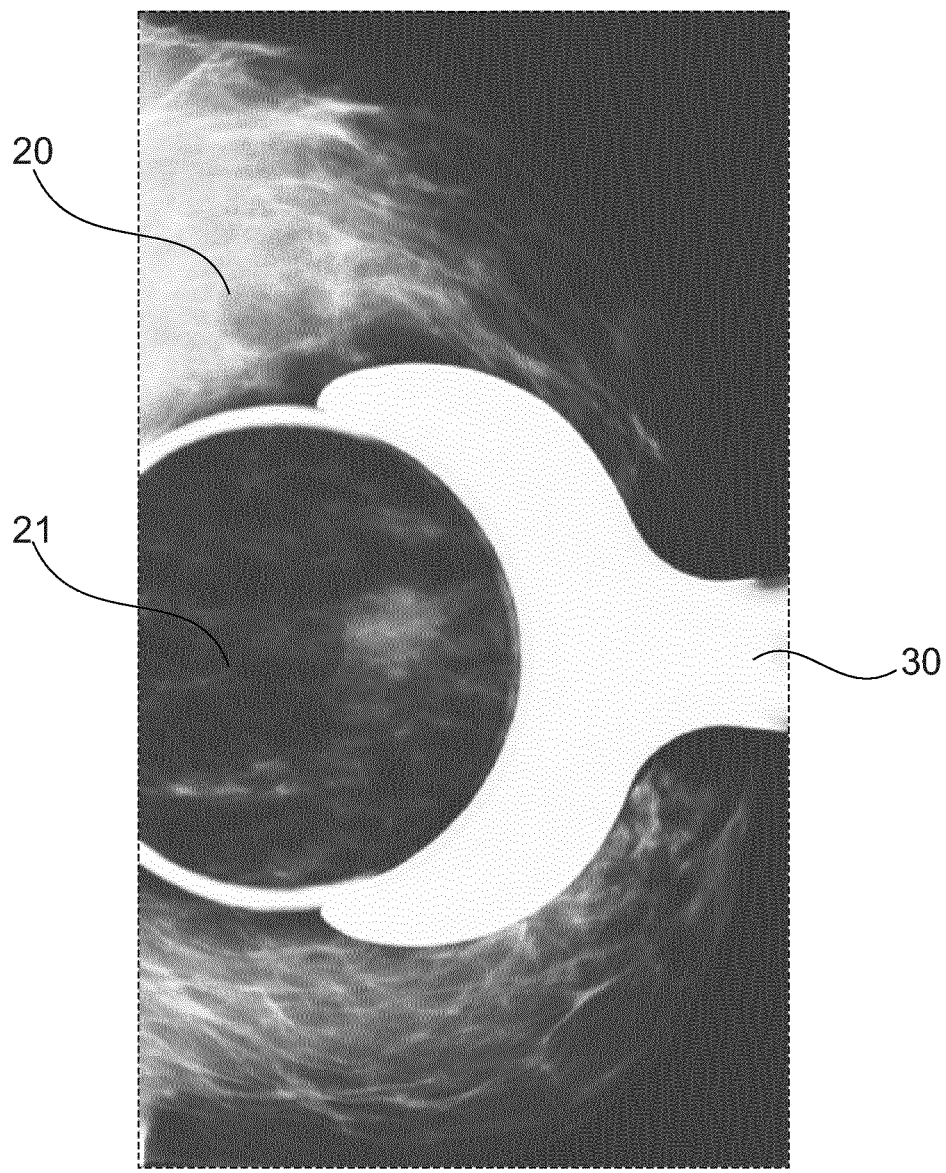
FIG. 1 is a schematic drawing of an X-ray image showing a breast examined by a device according to the prior art.

FIG. 1 is a schematic drawing of an X-ray image showing a breast 20 examined by a device according to the prior art. FIG. 1 shows the breast 20 to be examined. Only a part of the breast 20 is a region of interest 21. Only this part of the breast 20 is locally compressed by a spot compression device 30 according to the prior art. Despite, the entire breast 20 is visible in the X-ray image, which means the entire breast 20 is, according to the prior art, unnecessarily exposed to X-ray radiation.

Figure 2:
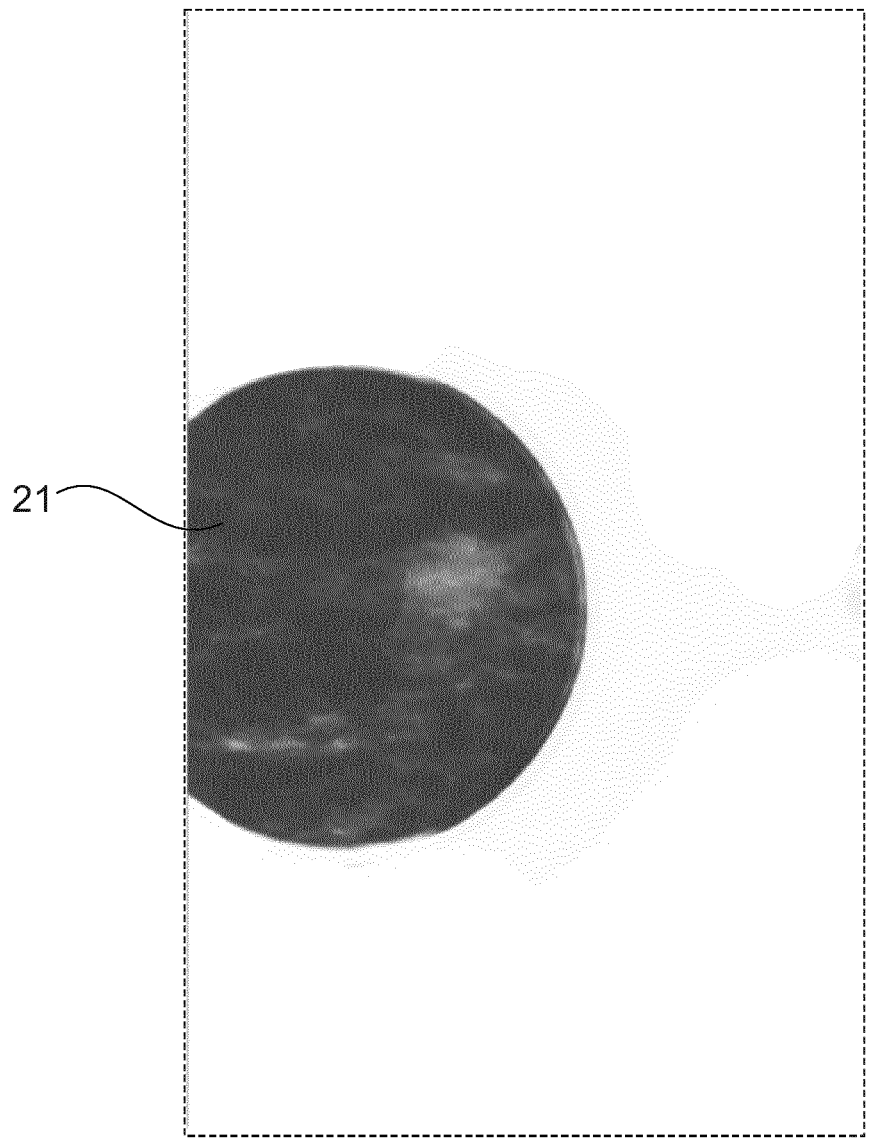
FIG. 2 is a schematic drawing of an X-ray image showing a breast examined by a compression and shielding device according to the present invention.

FIG. 2 is a schematic drawing of an X-ray image showing a part of a breast examined by a compression and shielding device according to the present invention. FIG. 2 shows only the relevant part of the breast which is the region of interest 21 and which is locally compressed by a compression element according to the present invention. The image differs from the image of FIG. 1 by showing a sharp contrast around the compressed portion of the breast. Further in contrast to FIG. 1, not the entire breast is visible in the X-ray image. This means that not the entire breast is unnecessarily exposed to X-ray radiation, but only the relevant part of the breast which is the region of interest 21.

Figure 3:
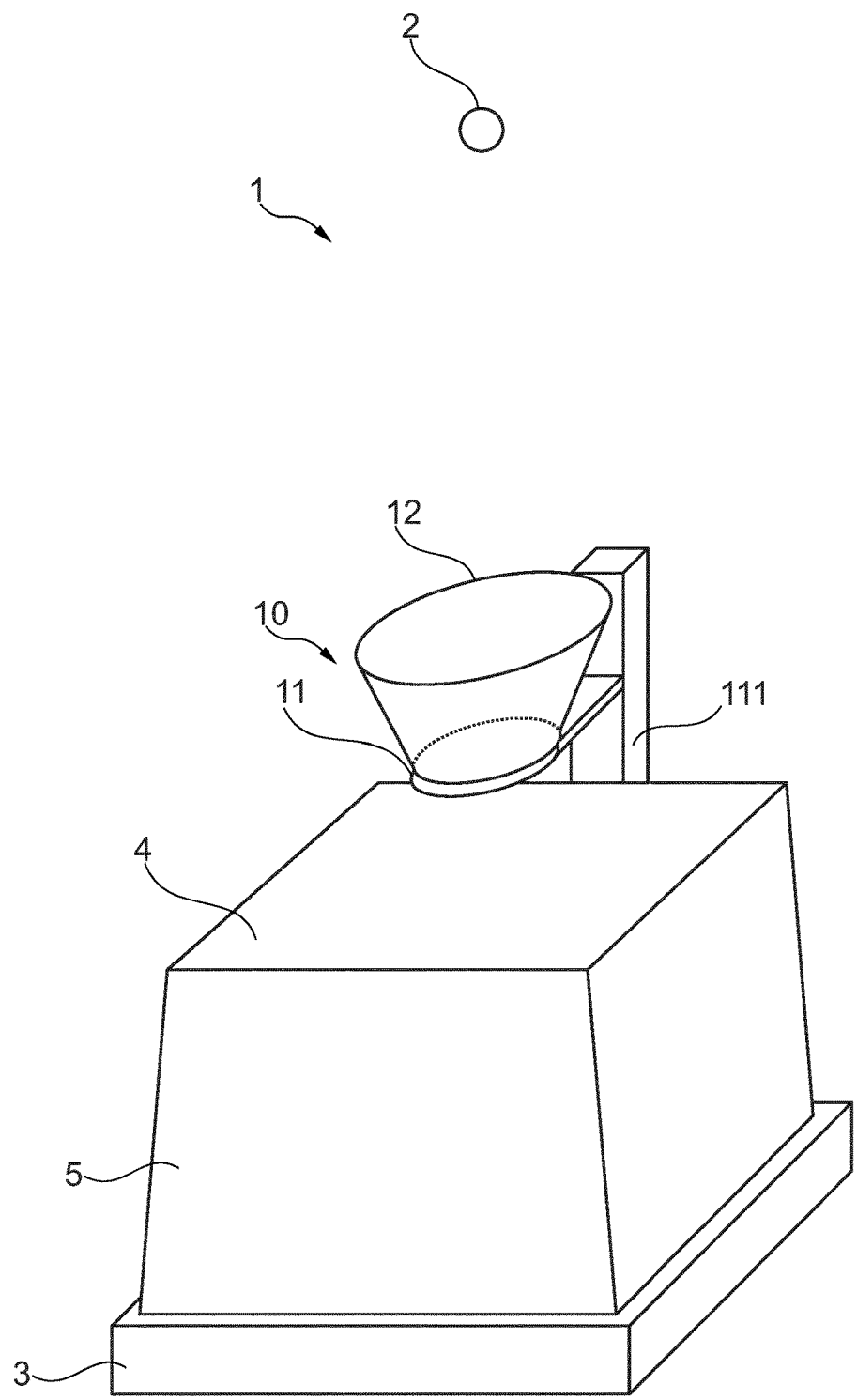
FIG. 3 is a schematic drawing of an example of an X-ray mammography system according to the present invention.

FIG. 3 shows a schematic drawing of an example of an X-ray mammography system 1 according to the present invention. The X-ray mammography system 1 comprises an X-ray source 2, an X-ray detector 3, a breast support 4, a positioning element 5, a compression element 11, and a shielding 12. The compression element 11 and the shielding 12 form a compression and shielding device 10 for X-ray mammography according to the present invention.

The X-ray source 2 is arranged above an area where a breast to be examined can be positioned. The X-ray source 2 is arranged to direct X-ray radiation to a breast to be examined. The X-ray detector 3 is arranged below the breast (now shown) to detect X-ray radiation having passed through the breast to be examined.

The breast support 4 is arranged to support the breast to be examined. The breast support 4 is a breast support table. Below the breast support 4, a positioning element 5 is arranged. Here, the positioning element 5 is integrated into the breast support 4. The positioning element 5 is movable towards the X-ray source 2 from a lower to an upper position. By moving the positioning element 5 and thereby the breast support table towards the X-ray source 2 into the upper position, the breast is lifted towards the X-ray source 2, which allows a magnification image of the breast compared to lower position. In other words, the positioning element 5 positions the breast closer to the X-ray source 2 than without the positioning element 5.

The compression element 11 is arranged to compress a part of the breast to be examined. The shielding 12 is arranged between the X-ray source 2 and the compression element 11 to shield an uncompressed part of the breast from the X-ray radiation. The shielding 12 is further formed to allow the direction of X-ray radiation to the compressed part of the breast and to keep an uncompressed part of the breast uncovered.

In other words, a breast to be examined (not shown) will be positioned on top of the breast support 4 in form of a table. The breast will be compressed using the movable compression element 11 that is attached to an arm of a standard compression paddle 111. The shielding 12 arranged on top of the compression element 11 blocks X-ray radiation that could otherwise reach non-compressed breast parts.

The compression and shielding device 10 is formed to contact the breast to be examined only by the compression element 11 which comprise a circumferential edge to contact the breast.

The compression element 11 is a spot compression element to compress only a part of the breast to be examined. It is circular, disc-shaped and transparent to X-ray radiation.

The shielding 12 is connected with the compression element 11 and cone shaped. The cone shaped shielding 12 extends in the direction of the X-ray source 2 in order to block the uncompressed parts of the breast from being exposed to X-ray radiation. The shielding 12 has to be composed from a material that is opaque to X-ray radiation.

The compression and shielding device 10 allows extremely low dose acquisitions by shielding uncompressed parts of the breasts from radiation. Thereby, the total dose for this type of examination is minimized.

Figure 4:
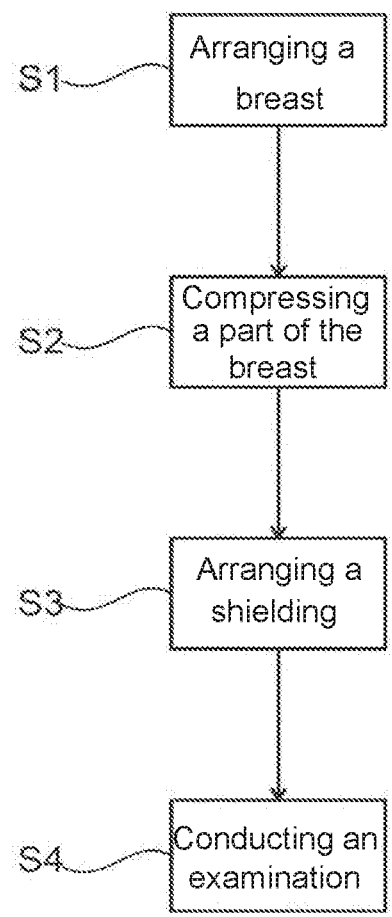
FIG. 4 is a schematic drawing of an example of a method for X-ray mammography according to the present invention.

FIG. 4 shows a schematic drawing of an example of a method for X-ray mammography according to the present invention. The method for X-ray mammography comprises the steps of:

Step S1, arranging a breast to be examined on a breast support 4,

Step S2, compressing a part of the breast to be examined in a compression element 11, Step S3, arranging a shielding 12 between an X-ray source 2 and the compression element 11 to shield an uncompressed part of the breast from the X-ray radiation, and Step S4, conducting an examination of the compressed part of the breast.

The shielding 12 is arranged between the X-ray source 2 and the compression element 11 to shield an uncompressed part of the breast from the X-ray radiation. The shielding 12 is further formed to allow the direction of X-ray radiation to the compressed part of the breast and to keep an uncompressed part of the breast uncovered.

The compression and shielding device for X-ray mammography, the X-ray mammography system, and the method for X-ray mammography according to the present invention are also suitable for other radiation than X-ray, as e.g. acoustic radiation and electromagnetic radiation in the near ultraviolet, visible, infrared and microwave regions.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A compression and shielding device for X-ray mammography, comprising:
   a compression element, and
   a shielding,
   wherein the compression element is arranged to compress a part of a breast to be examined, and
   wherein the shielding is to be arranged between an X-ray source and the compression element to shield an uncompressed part of the breast from X-ray radiation, and is formed to allow the direction of X-ray radiation to the compressed part of the breast and to keep an uncompressed part of the breast uncovered.

2. The device according to claim 1, which is formed to contact the breast to be examined only by the compression element.

3. The device according to claim 1, wherein the compression element comprises a circumferential edge to contact the breast to be examined.

4. The device according to claim 1, wherein the compression element is disc-shaped.

5. The device according to claim 1, wherein the compression element is a spot compression element suitable to compress only a part of the breast to be examined.

6. The device according to claim 1, wherein the compression element is transparent to X-ray radiation.

7. The device according to claim 1, wherein the shielding is connected with the compression element.

8. The device according to claim 1, wherein the shielding is cone shaped.

9. The device according to claim 1, wherein the shielding is opaque to X-ray radiation.

10. An X-ray mammography system, comprising:
    an X-ray source,
    an X-ray detector,
    a breast support,
    a compression element, and
    a shielding,
    wherein the X-ray source is arranged to direct X-ray radiation to a breast to be examined,
    wherein the X-ray detector is arranged to detect X-ray radiation having passed through the breast to be examined,
    wherein the breast support is arranged to support the breast to be examined,
    wherein the compression element is arranged to compress a part of the breast to be examined, and
    wherein the shielding is arranged between the X-ray source and the compression element to shield an uncompressed part of the breast from the X-ray radiation, and is formed to allow the direction of X-ray radiation to the compressed part of the breast and to keep an uncompressed part of the breast uncovered.

11. The system according to claim 10, wherein the breast support comprises a positioning element to position the breast closer to the X-ray source than without the positioning element.

12. A method for X-ray mammography, comprising:
    arranging a breast to be examined on a breast support,
    compressing a part of the breast to be examined in a compression element,
    arranging a shielding between an X-ray source and the compression element to shield an uncompressed part of the breast from X-ray radiation, and
    conducting an examination of the compressed part of the breast,
    wherein the shielding is arranged between the X-ray source and the compression element to shield the uncompressed part of the breast from the X-ray radiation, and is formed to allow the direction of X-ray radiation to the compressed part of the breast and to keep the uncompressed part of the breast uncovered.

* * * * *